United States Patent
Gjata et al.

(10) Patent No.: US 6,471,436 B1
(45) Date of Patent: *Oct. 29, 2002

(54) ELASTOMERIC CONNECTOR COUPLING MOTOR TO CAM ACTUATOR OF INFUSION PUMP

(75) Inventors: John D. Gjata, Leucadia, CA (US); Michael W. Lawless, Poway, CA (US); Andrew J. Scherer, San Demas, CA (US); Peter A. Soberon, San Diego, CA (US); Stephanie R. Squarcia, Palo Alto, CA (US)

(73) Assignee: Abbott Laboratories, Abbott Park, IL (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/100,621

(22) Filed: Jun. 19, 1998

(51) Int. Cl.[7] ................................................. F16D 1/00
(52) U.S. Cl. ........................ 403/223; 403/305; 403/228; 464/87
(58) Field of Search ................................. 403/305, 301, 403/300, 383, 359.6, 220, 221, 223, 228; 464/87, 88, 89

(56) References Cited

U.S. PATENT DOCUMENTS

| | | | |
|---|---|---|---|
| 2,297,619 A | | 9/1942 | Haberstump |
| 2,857,749 A | * | 10/1958 | Fabbri et al. ................. 464/88 |
| 2,898,751 A | * | 8/1959 | Bromley ....................... 464/88 |
| 3,057,647 A | | 10/1962 | Wood |
| 3,423,957 A | * | 1/1969 | Palmer ......................... 464/88 |
| 4,391,600 A | | 7/1983 | Archibald |
| 5,347,881 A | * | 9/1994 | Watson et al. ........... 403/305 X |
| 5,586,868 A | | 12/1996 | Lawless et al. |

* cited by examiner

Primary Examiner—Lynne H. Browne
Assistant Examiner—John R. Cottingham
(74) Attorney, Agent, or Firm—Beth A. Vrioni

(57) ABSTRACT

A drive connector for elastomerically coupling a drive shaft to a driven shaft. An elastomeric coupling includes openings on opposite ends that are generally "D"-shaped forming an interference fit with correspondingly shaped ends of the drive shaft and the driven shaft. A web extends transversely within the interior of the elastomeric coupling, limiting the distance that the drive shaft and driven shaft are inserted within the openings of the coupling. The coupling includes a rib that runs longitudinally along its outer length. A sleeve having a groove corresponding in size and shape to the rib is slipped over the coupling and is connected to the driven shaft. The sleeve includes a rigid interior element that is overmolded with an elastomeric material. A cam bearing is fitted over a cam surface on the sleeve and provides a force in one direction, urging a plunger to displace an elastomeric membrane in a pumping cassette, forcing medicinal fluid to flow through the pumping cassette. The elastomeric membrane provides the restoring force to the plunger, so that a loop formed on the upper portion of the plunger and disposed around the cam bearing does not receive any force from the cam bearing to move the plunger away from the pump cassette. The elastomeric coupling and sleeve form a relatively compact assembly for coupling the drive shaft to the driven shaft and accommodate minor misalignment between the center lines of the drive shaft and the driven shaft.

6 Claims, 4 Drawing Sheets

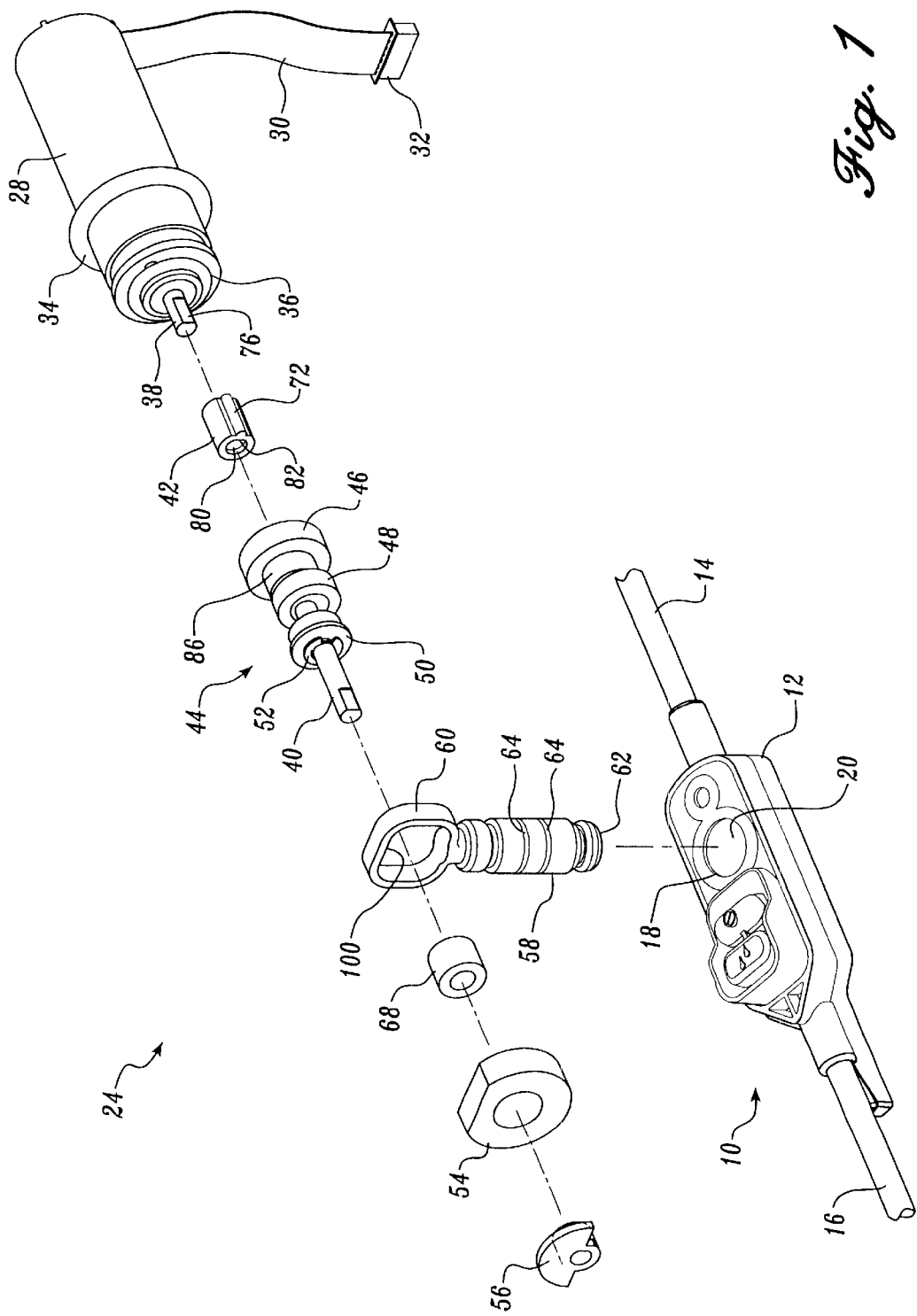

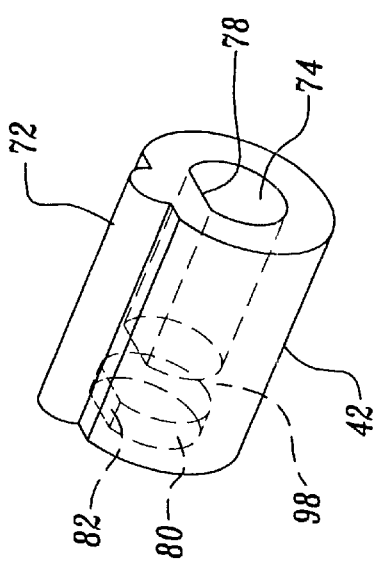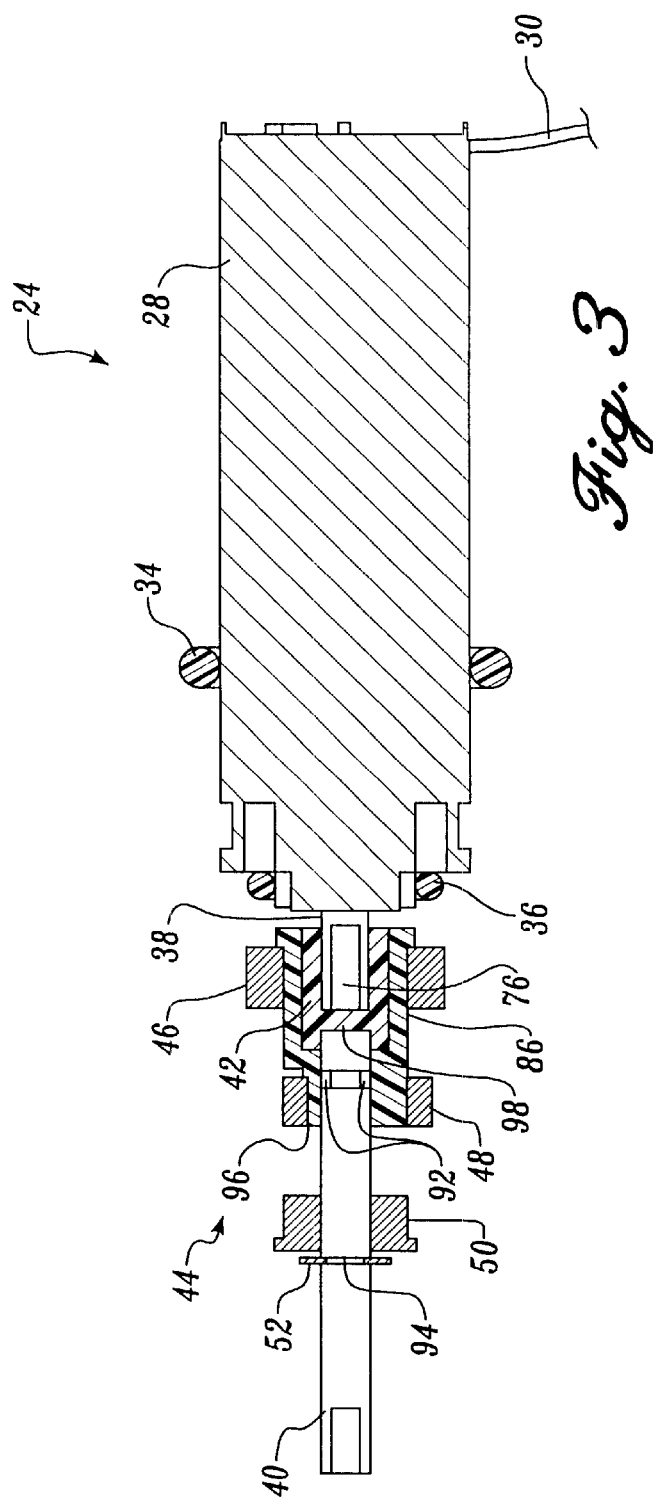

ELASTOMERIC CONNECTOR COUPLING MOTOR TO CAM ACTUATOR OF INFUSION PUMP

FIELD OF THE INVENTION

This invention generally pertains to a connector for use in coupling a motor drive shaft to a driven shaft, and more specifically, in a medical drug infusion pump, to an elastomeric coupler for connecting a motor drive shaft to a cam shaft that drives a plunger in the pump, and to providing a restoring force for the plunger.

BACKGROUND OF THE INVENTION

In many portable motor driven devices, small direct current (DC) motors are connected to rotatably driven shafts using solid metal couplers. Such couplers comprise a short section of thick-walled tubing having two threaded orifices in the tubing wall, adjacent each end. A set screw is threaded into each orifice. The set screws are tightened to engage a drive shaft of the motor that is inserted into one end of the coupler, and to secure a driven shaft that is inserted into the other end of the coupler. Even if a fastener locking substance is applied, the set screws often loosen with use, causing scoring of the shafts and possible failure of the devices in which the couplers are installed.

Couplers are generally available from suppliers in only a limited range of sizes. If the coupler used to join two shafts is too large, it will not properly connect the shafts and can cause vibration, because its mass is not symmetrically distributed around the center lines of the two shafts. In addition, conventional couplers generally require that the center lines of the two shafts that are joined be relatively closely aligned. Thus, for example, any misalignment between a motor drive shaft and a driven shaft, even if slight, is likely to cause side loading of one or both shafts, producing greater bearing wear. Solid couplers also transmit noise and vibration from the motor to other parts of the device in which they are used.

Ideally, it would be preferable to provide a more flexible coupling between a motor drive shaft and a driven shaft. Large motor couplers sometimes include fiber reinforced rubber assemblies clamped around the ends of two shafts to provide some degree of flexibility, but such couplers are too large for use in small devices.

It will therefore be apparent that a simple coupler, which addresses the problems noted above and is relatively low in cost, would be desirable for use in small electric motor powered devices. The prior art does not provide a suitable alternative to the prior art solid metal connector of the type described, or the too large and cumbersome prior art fiber reinforced rubber connector assemblies.

SUMMARY OF THE INVENTION

In accord with the present invention, a coupler is defined for connecting a non-cylindrical end of a drive shaft to a non-cylindrical end of a driven shaft. The coupler includes a generally cylindrical fitting having opposed first and second ends. A first opening is disposed at the first end of the fitting, and a second opening is disposed at the second end of the fitting. The first opening has a size and a shape generally corresponding to a size and a shape of the non-cylindrical end of the drive shaft. Likewise, the second opening has a size and a shape generally corresponding to a size and a shape of the non-cylindrical end of the driven shaft. The fitting is formed of an elastomeric material adapted to elastically stretch when the first opening is forced over the drive shaft and when the second opening is forced over the driven shaft, providing an interference fit in each case. The fitting is thereby adapted to drivingly couple the drive shaft to the driven shaft.

Preferably, the fitting further comprises a web that is disposed transverse to a longitudinal axis of the fitting, between the first opening and the second opening. This web limits a depth to which the drive shaft and the driven shaft are advanced into the first opening and the second opening, respectively. Also, the web limits vibration of the drive shaft propagating into the driven shaft from the drive shaft.

A sleeve that is sized to snugly fit around an outer surface of the fitting in an interference fit provides a compression force that helps to keep the fitting seated on the drive shaft. An outer surface of the sleeve includes a cam surface adapted to act on a plunger. As the drive shaft rotates the driven shaft, the sleeve causes the plunger to move along a longitudinal axis of the plunger. Preferably, the cam surface is adapted to only apply a force against the plunger in one direction; the plunger is biased in an opposite direction by an elastomeric membrane which the plunger displaces.

An outer surface of the fitting is keyed to an inner surface of the sleeve. Also, an inner surface of the first opening includes a flat section adapted to seat on a corresponding flat section formed on the end of the drive shaft. In a similar manner, an inner surface of the second opening includes a flat section adapted to seat on a corresponding flat section formed on the end of the driven shaft.

The elastomeric fitting thus minimizes vibration transmission between the drive shaft and the driven shaft and helps to minimize audible noise. Because of its elasticity, the fitting can accommodate at least a limited degree of misalignment between the drive shaft and the driven shaft.

BRIEF DESCRIPTION OF THE DRAWING FIGURES

The foregoing aspects and many of the attendant advantages of this invention will become more readily appreciated as the same becomes better understood by reference to the following detailed description, when taken in conjunction with the accompanying drawings, wherein:

FIG. 1 is an exploded isometric view of a motor and drive assembly in accord with the present invention, and illustrates a pump cassette through which medicinal fluid is pumped by a plunger actuated by the drive assembly;

FIG. 2 is an isometric view of an elastomeric coupler for coupling a drive shaft to a driven shaft;

FIG. 3 is a cross section elevational view of a portion up the drive assembly;

DESCRIPTION OF THE PREFERRED EMBODIMENT

An exemplary application of the present invention is illustrated for use in pumping a medicinal fluid through a pump cassette 10, as shown in FIG. 1. Pump cassette 10 is disposable, being intended for use with a single patient.

Figure 6:
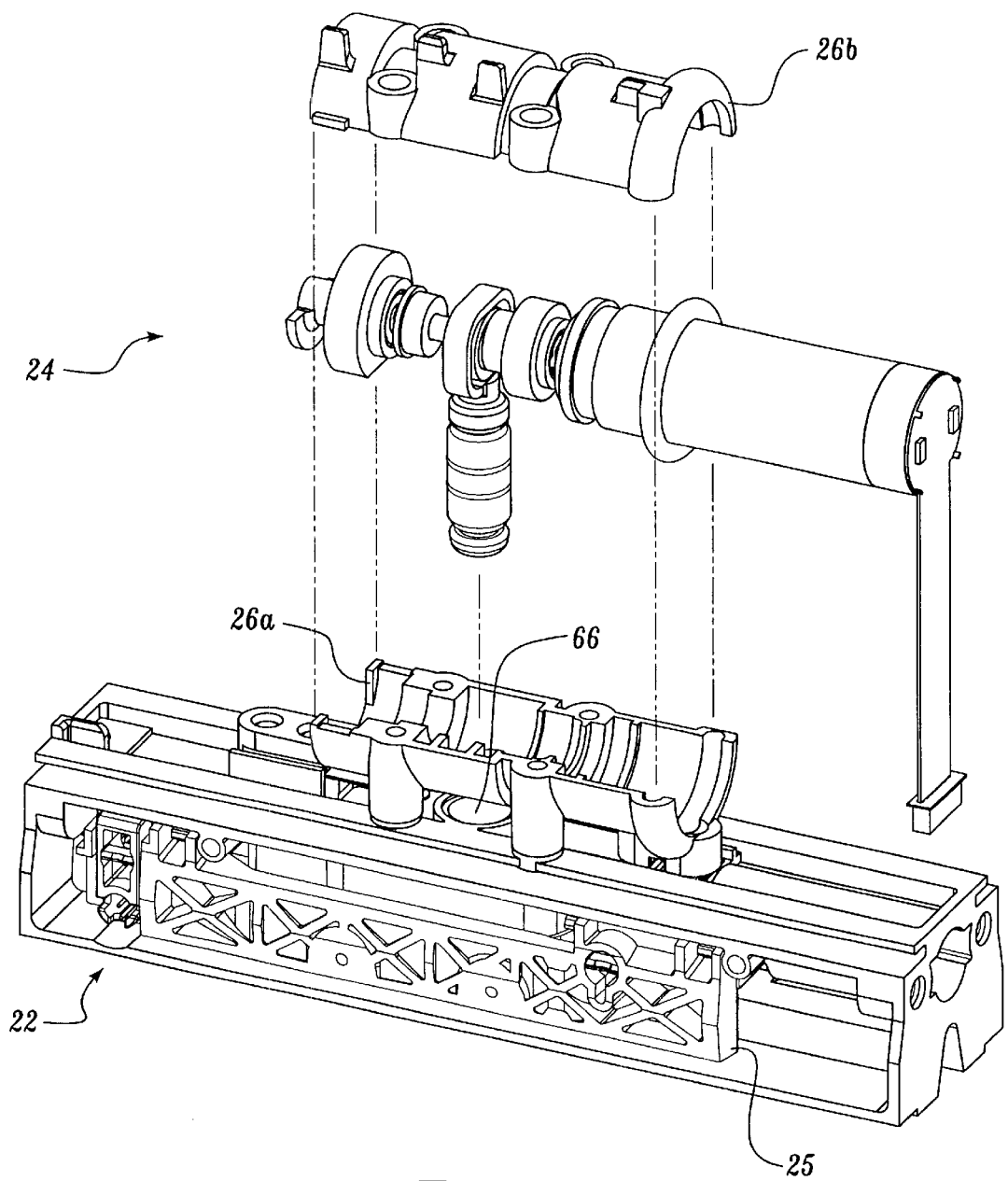
FIG. 6 is an exploded isometric view of the motor, drive assembly, plunger, and pump chassis.

Details of the pump cassette are disclosed in commonly assigned U.S. Pat. No. 5,586,868, the drawings and specification of which are hereby specifically incorporated herein by reference. Proximal tubing 14 and distal tubing 16 are coupled to the proximal and distal ends of the pump cassette. A reservoir (not shown) of medicinal fluid is connected to proximal tubing 14, while distal tubing 16 is connected into a patient's cardiovascular system to infuse the medicinal fluid at a rate determined by the speed with which pump cassette 10 is driven. Pump cassette 10 includes a plastic housing 12 having an opening 18 formed in an upper surface thereof. Opening 18 exposes an elastomeric membrane 20, which is sealed between the top and bottom portions of the plastic housing. The undersurface of elastomeric membrane 20 is exposed to a fluid path through pump cassette 10 and is operative to displace the medicinal fluid when elastomeric membrane 20 is forced inwardly into the interior of pump cassette 10. The pump cassette is latched into a pump chassis 22, which is shown in FIG. 6. The pump chassis is mounted in a pump housing (not shown) which includes a battery supply, electronic components for controlling the pumping action, and a user interface, none of which are shown. A pivotal member 25 on pump chassis 22 is spring biased to engage housing 12 of pump cassette 10 to latch it in a predefined position within the pump chassis. Details of this latching mechanism and other aspects of pump chassis are not pertinent to the present invention, and therefore are not disclosed herein.

Figure 4:
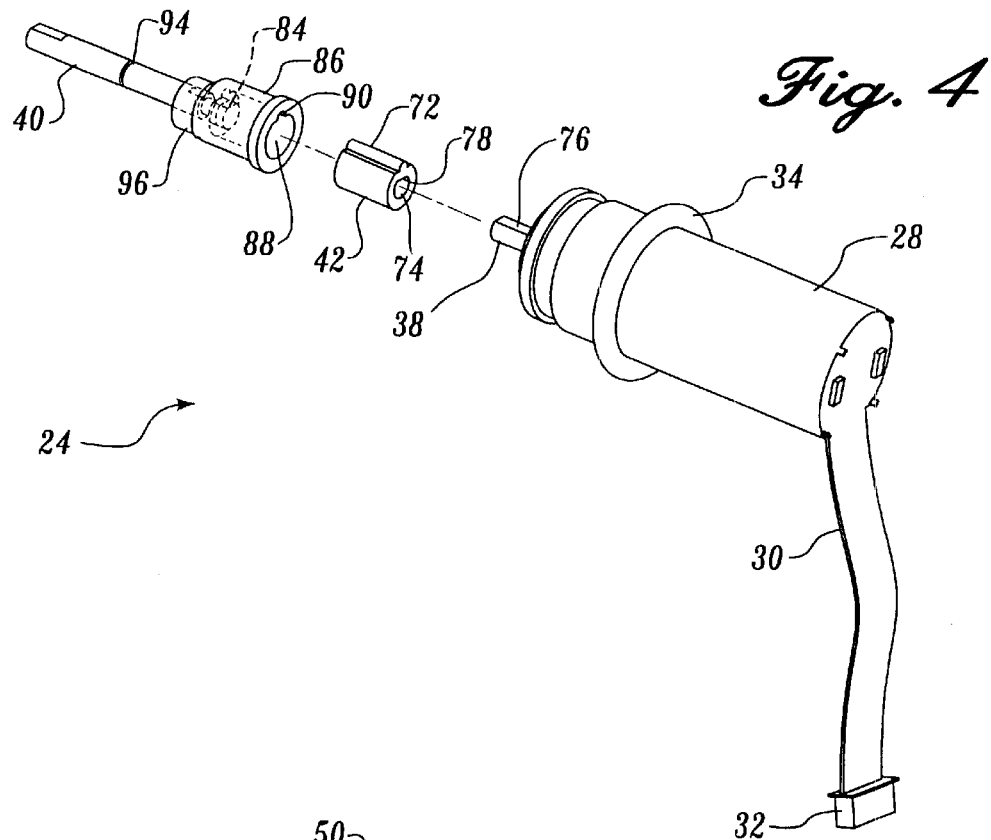
FIG. 4 is an exploded isometric view showing the motor and a portion of the drive assembly.
Figure 5:
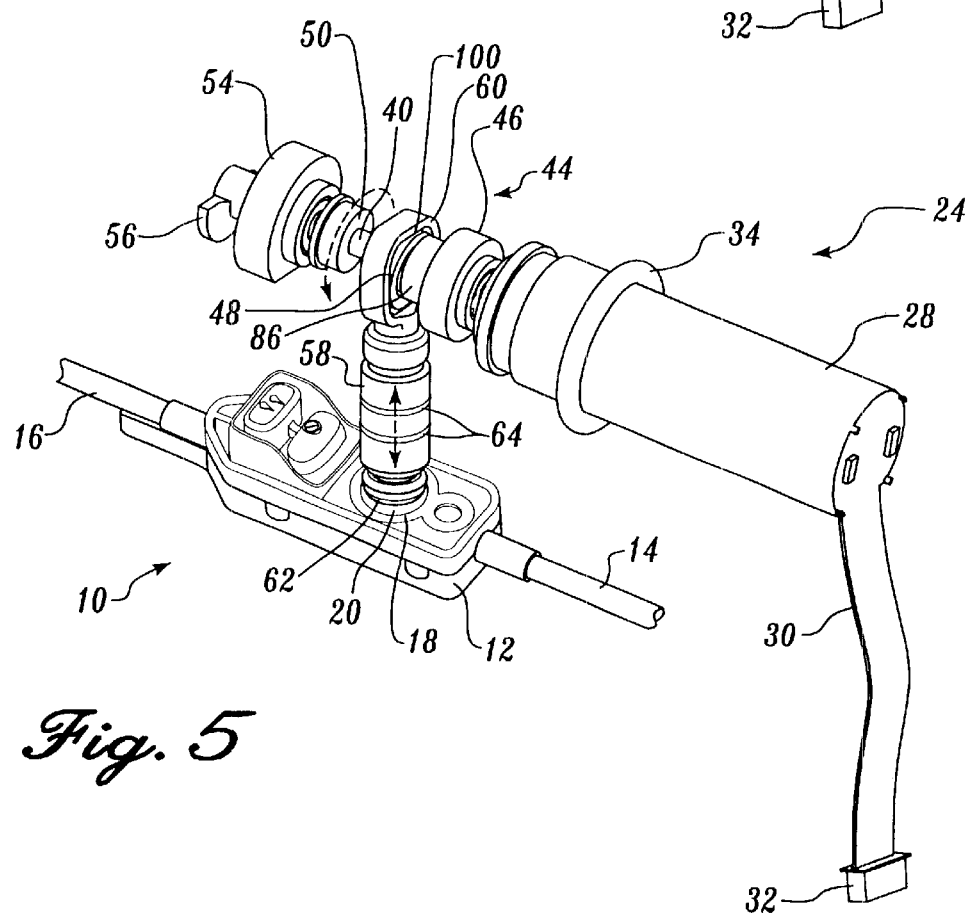
FIG. 5 is an isometric view of the motor, drive assembly, plunger, and pump cassette.

A drive assembly 24 provides the force that deflects elastomeric membrane 20 into the interior of pump cassette 10 to pump medicinal fluid into the patient's body. Further details of the drive assembly and its interaction with the pump cassette are illustrated in FIGS. 3, 4, and 5. Drive assembly 24 includes a DC motor 28 that is energized with an electrical current provided through a flex lead 30, which has a connector plug 32 adapted to couple to a mating connector on a printed circuit board (neither shown) within the interior of the pump. A resilient O-ring support 34 is provide around the outer surface of motor 28 and is seated within a pair of drive enclosure shells 26a and 26b, which are fastened around the drive assembly to enclose and support it, generally as illustrated in FIG. 6. A second resilient O-ring support 36 is disposed at the end of DC motor 28, providing further support to the motor and drive assembly within drive enclosure shells 26a and 26b. Just beyond O-ring 36, a drive shaft 38 extends from the end of DC motor 28 and is connected with a coupling 42 comprising an elastomeric material. Coupling 42 is also connected to a driven shaft 40 and is operative to transmit the rotational force from drive shaft 38 to driven shaft 40.

Internal details of coupling 42 are illustrated in FIG. 2. As shown therein and in FIGS. 1 and 4, a portion of drive shaft 38 that is connected to coupling 42 has a flat 76 on one side so that it is generally "D"-shaped. This portion of drive shaft 38 extends into an opening 74 in coupling 42. Opening 74 also has a flat 78 on a portion of its circumference, so that its shape is also "D"-shaped, but slightly smaller in size than the end of drive shaft 38. Thus, coupling 42 forms an interference fit with drive shaft 38 when the end of the drive shaft is inserted into opening 74 of the coupling. At the opposite end of coupling 42 from opening 74 is disposed an opening 80 having a flat 82 on one side and therefore also being generally "D"-shaped in cross section. A flat 84 is formed on the end of driven shaft 40, so that it is also "D"-shaped, but slightly larger in size than opening 80. Thus, an interference fit is also provided when driven shaft 40 is inserted into opening 80 of coupling 42. A transverse web 98 (shown in FIG. 2) is disposed within coupling 42, separating opening 74 from opening 80 and limiting the extent to which drive shaft 38 and driven shaft 40 extend within coupling 42. Transverse web 98 also limits the transmission of vibration from drive shaft 38 to driven shaft 40, since it prevents the ends of the drive shaft and driven shaft from contacting each other.

The exterior surface of coupling 42 is generally cylindrical, but on one side, a rib 72 extends generally parallel to the longitudinal axis of the coupling. Rib 72 has a semicircular cross section. Since the coupling is made of a elastomeric material, i.e., preferably from a synthetic rubber, it is possible that either or both drive shaft 38 or driven shaft 40 might rotate within the coupling by distorting the coupling. To prevent such distortion and consequential slippage, a sleeve 86 is provided. The sleeve extends over the outer surface of coupling 42, in a snug fit, creating a compressive force that precludes either of the shafts distorting the coupling sufficiently to rotate within the "D"-shaped openings formed in the ends of the coupling. Sleeve 86 has an opening 88 with an internal diameter approximately equal to the external diameter of coupling 42. Further, a longitudinally extending notch 90 having a cross-sectional profile and size corresponding to that of rib 72 is formed on one side of opening 88 to receive the rib when sleeve 86 is slipped over coupling 42. It will be apparent that coupling 42 could alternatively be provided with a notch to receive a correspondingly shaped and sized rib formed on the inner surface of the opening into sleeve 86, to key the coupling and sleeve. In a preferred embodiment, sleeve 86 is an overmolded component that includes a rigid internal element (not shown) formed of a hard plastic or metal material, which is coated or overmolded with an elastomeric material—preferably synthetic rubber.

Just behind flat 84 on driven shaft 40 is disposed a circular groove 92 (see FIG. 3) that engages the internal elastomeric portion of sleeve 86 so that the sleeve is affixed to the end of driven shaft 40, which is connected to coupling 42. Sleeve 86 is also prevented from rotating about driven shaft 40 by its interference fit over flat 84 on the driven shaft. Use of sleeve 86 thus assists in transmitting the rotational force from drive shaft 38 to driven shaft 40.

Several significant advantages are derived from the use of coupling 42 to connect drive shaft 38 and driven shaft 40. Due to the elastomeric nature of coupling 42, the coupling allows for some misalignment between the center lines of drive shaft 38 and driven shaft 40 and thus decreases side loading on either the driven shaft or the drive shaft. The decrease in side loading improves the operating life of the drive assembly, in particular, the life of bearings 46 and 50. Further, the decrease in side loading increases the operating life of the motor and enables a lower cost motor to be used, since less expensive bearings are required on the drive shaft of the motor than would be required to handle higher side loading. In addition, coupling 42 eliminates the need for mechanical fasteners to attach drive shaft 38 to driven shaft 40 and decreases the noise level of the drive assembly, since vibration in the motor is at least partially isolated from components of the drive assembly that are downstream of coupling 42. Compared to prior art devices for coupling a drive shaft to a driven shaft, coupling 42 is relatively smaller and compact. Furthermore, assembly of the coupling and sleeve is relatively simple, so that a decrease in assembly time and the number of parts, and a corresponding resultant cost reduction in the drive assembly is achieved by using coupling 42 and sleeve 86 rather than a prior art type coupling.

Sleeve 86 serves yet a further purpose in this exemplary application of the present invention. Specifically, sleeve 86 includes a cam surface 96, which defines a profile having a locus of points at a varying radial distance from a center line of driven shaft 40. As drive shaft 38 rotates driven shaft 40 and sleeve 86, cam surface 96 is rotated. The rotating cam surface applies a force that is used to displace a plunger 58, causing it to move toward the pump cassette. A plunger foot 62 is formed on the end of plunger 58 and is in contact with elastomeric membrane 20 in pump cassette 10. Plunger 58 includes two O-rings 64 that seal against the internal surface of an opening 66 in pump chassis 22 (FIG. 6), thereby helping to prevent water and other liquids from entering the interior of the pump housing.

Cam surface 96 is formed on only a portion of the outer surface of sleeve 86. The portion of sleeve 86 that does not include cam surface 96 is radially equidistant from the center line of driven shaft 40. A bearing 46 is seated on this portion of sleeve 86 and assists in supporting the drive assembly during rotation of the drive shaft and driven shaft.

As shown in FIGS. 1,3, and 5, drive assembly 24 also includes a bearing 50 around driven shaft 40. Bearing 50 is held in place by a clip 52 that fits within an annular groove 94 formed on driven shaft 40 (see FIG. 3). Beyond clip 52 on drive shaft 40 is disposed a clutch assembly 54. Clutch assembly 54 includes a roller clutch 68. At the end of driven shaft 40 that is remote from sleeve 86 is disposed an encoder tab 56. The encoder tab is used for determining a home position of driven shaft 40 for purposes of controlling the drive assembly and for other purposes not related to the present invention.

A cam bearing 48 is disposed around cam surface 96 and comprises a radial ball type bearing; this cam bearing serves as a friction reducing interface between cam surface 96 and a loop 60 formed on the end of plunger 58 that is opposite the end on which plunger foot 62 is disposed. Loop 60 is generally shaped like a square with rounded corners. The radially outer surface of cam bearing 48 does not contact an inner portion 100 of loop 60, since cam surface 96 does not apply any force to plunger 56 that would move the plunger away from elastomeric membrane 20. Instead, the elastomeric membrane provides a restoring force that lifts plunger 56 upwardly, away from the interior of pump cassette 10. Cam bearing 48 contacts other inner portions of loop 60 and provides the force that drives plunger 56 toward pump cassette 10, to displace elastomeric membrane 20 into the interior of the pump cassette and thereby forces the medicinal liquid to flow through distal line 16. The clearance between cam bearing 48 and surface 100 of loop 60 is only a few mils, but is sufficient to prevent any scrubbing action between the outer surface of the cam bearing and the inner surface of the loop that would reduce the efficiency with which plunger 56 is driven by drive assembly 24.

Although the present invention has been described in connection with the preferred form of practicing it, those of ordinary skill in the art will understand that many modifications can be made thereto within the scope of the claims that follow. Accordingly, it is not intended that the scope of the invention in any way be limited by the above description, but instead be determined entirely by reference to the claims that follow.

What is claimed:

1. A resilient coupling assembly for transmitting a rotational drive force from a first shaft to a second shaft, comprising:
   (a) a generally elongate elastomeric member having:
      (i) a first orifice disposed at one end of the elastomeric member and sized to provide an interference fit over the first shaft; and
      (ii) a second orifice disposed at an opposite end of the elastomeric member and sized to provide an interference fit over the second shaft; and
   (b) an elongate sleeve having a central opening that is sized to provide an interference fit over an outer surface of the elastomeric member and providing a compressive force against the elastomeric member that retains the elastomeric member on at least one of the first and the second shafts, so that the shafts are coupled together through the elastomeric member; wherein an outer surface of the sleeve comprises a cam surface having a profile that defines a locus of points at a varying radius about a central axis of the elastomeric member; and
   (c) a link having a generally quadrilateral opening through which the sleeve extends, said link riding against the cam surface of the sleeve as the sleeve rotates.

2. The resilient coupling assembly of claim 1, wherein the elastomeric member includes a web that extends transversely and is disposed between the first orifice and the second orifice.

3. The resilient coupling assembly of claim 1, wherein at least one of the sleeve and the outer surface of the elastomeric member includes an alignment groove to key the position of the driven shaft.

4. The resilient coupling assembly of claim 3, wherein another of the sleeve and the outer surface of the elastomeric member includes an alignment ridge, sized to fit within the alignment groove, said alignment groove and alignment ridge cooperating together to provide the interference fit between the elastomeric member and the sleeve.

5. The resilient coupling assembly of claim 1, wherein the link is coupled to a plunger that is driven to move in a direction away from the sleeve as the cam surface rides against one side of the quadrilateral opening.

6. A resilient coupling assembly for transmitting a rotational drive force from a first shaft to a second shaft, comprising:
   (a) a generally elongate elastomeric member having:
      (i) a first orifice disposed at one end of the elastomeric member and sized to provide an interference fit over the first shaft; and
      (ii) a second orifice disposed at an opposite end of the elastomeric member and sized to provide an interference fit over the second shaft; and
   (b) an elongate sleeve having a central opening that is sized to provide an interference fit over an outer surface of the elastomeric member and providing a compressive force against the elastomeric member that retains the elastomeric member on at least one of the first and the second shafts, so that the shafts are coupled together through the elastomeric member, wherein the sleeve comprises an elastomeric material that is overmolded onto a rigid material.

\* \* \* \* \*